United States Patent [19]

Kass

[11] Patent Number: 4,714,606
[45] Date of Patent: Dec. 22, 1987

[54] METHOD OF STAINING AND IDENTIFYING CELLS AND COMPOSITIONS THEREOF

[75] Inventor: Lawrence Kass, Hinckley, Ohio

[73] Assignee: Cytocolor Incorporated, Hinckley, Ohio

[21] Appl. No.: 765,348

[22] Filed: Aug. 13, 1985

Related U.S. Application Data

[63] Continuation-in-part of Ser. No. 610,381, May 15, 1984, abandoned, which is a continuation-in-part of Ser. No. 494,971, May 16, 1983, abandoned.

[51] Int. Cl.$^4$ .................. G01N 1/00; G01N 33/48
[52] U.S. Cl. .................................. 424/3; 424/7.1; 435/29; 435/34; 435/39; 534/611
[58] Field of Search .................. 436/63, 903; 435/29, 435/34, 39; 424/3, 7.1; 356/39; 534/607, 611

[56] References Cited

U.S. PATENT DOCUMENTS

| 3,578,386 | 5/1971 | Kalopissis et al. | 534/611 |
| 4,400,370 | 8/1983 | Kass | 424/3 |
| 4,500,509 | 2/1985 | Kass | 424/3 |
| 4,581,223 | 4/1986 | Kass | 424/3 |

OTHER PUBLICATIONS

Color Index, Revised Third Edition, vol. 6, (1975), pp. 5088 and 6392.
Williams, et al., Methods in Immunology & Immunochemistry, vol. 2, Academic Press, New York, 1968, pp. 365–380.

Primary Examiner—Robert J. Warden
Assistant Examiner—Stephen C. Wieder
Attorney, Agent, or Firm—Pearne, Gordon, McCoy & Granger

[57] ABSTRACT

This invention is directed to the cytology of blood, bone marrow and lymph node cells and the method of differentiating, identifying and enumerating said cells among a plurality of cells of hematopoietic origin. More specifically, the invention is directed to the use of a single cationic sulfur-containing azo dye in solution capable of staining said cells in a fixative. The dye is a water soluble quaternary azo dye identified in the Color Index as Basic Blue 41 capable of staining a plurality of cells including malignant cells of hematopoietic origin wherein the stained cells acquire individual color characteristics permitting the differentiation, identification and enumeration of each stained cell. The stained cells obtained by the process of this invention have individual color characteristics which permit the identification and differentiation by use of various instruments including, for example, an image analyzer, microscope, photomicroscope, and the like.

29 Claims, 4 Drawing Figures

CELL CLASSIFICATION

ABSORBANCE

B CELL - DIFFUSE NUCLEAR CHROMATIN, BLUE CYTOPLASM, NO GRANULES

FIG. 1A

T-HELPER - SMALLER THAN B CELL, LARGE AGGREGATES OF NUCLEAR CHROMATIN, BLUE CYTOPLASM, NO GRANULES

FIG. 1B

T-SUPPRESSOR SMALLER THAN B CELL, LARGE AGGREGATES OF NUCLEAR CHROMATIN, FAINT BLUE CYTOPLASM, 2-10 SMALL PINK GRANULES

FIG. 1C

NK OR NATURAL KILLER - LARGE LYMPHOCYTE, NUCLEUS CONTAINS PROMINENT AGGREGATE OF CHROMATIN, FAINT BLUE VERY ABUNDANT CYTOPLASM 8-20 LARGE COARSE RED TO PURPLE GRANULES

FIG. 1D

METHOD OF STAINING AND IDENTIFYING CELLS AND COMPOSITIONS THEREOF

CROSS-REFERENCE TO RELATED APPLICATIONS

This application is a Continuation-In-Part of copending application U.S. Pat. Ser. No. 610,381, filed May 15, 1984 now abandoned which in turn is a Continuation-In-Part of U.S. Pat. Ser. No. 494,971, filed May 16, 1983 now abandoned.

BACKGROUND OF THE INVENTION

This invention relates to the use of a single, substantially pure, water soluble quaternary azo dye for the cytological preparation of a fixed biopsy specimen derived from human blood, bone marrow, lymph nodes and other specimen of hematopoietic origin. The use of a water soluble quaternary azo dye (identified in the Colour Index as Basic Blue 41) in accordance with this invention, is an advance over the prior art (Romanowsky and Malachowski) wherein a mixture of dyes were used for staining biopsy specimens. The stained cells of hematopoietic origin in accordance with this invention have excellent Colour stability and are remarkably clear with respect to cellular detail and brilliance of cell structure.

The use of the water soluble quaternary azo dye of this invention is an improvement over the above-mentioned Romanowsky stains even though the panoptic mixture of dyes are still the basis of morphological hematology and are presently being used for the identification of cells of hematopoietic origin including human blood cells, bone marrow cells, and lymph node cells.

Ehrlich introduced the use of dyes to effect or enhance cell differentiation in human biopsy specimens particularly blood cells. Ehrlich's dyes were superceded, however, by the use of mixtures of dyes identified as Romanowsky dyes which have been modified to include mixtures such as methylene blue, modified methylene blues, eosins, azures and methylene violet. These mixtures of dyes have been generally classified as panoptic stains because of the wide range and broad spectra of hues and chroma produced when reacted with a fixed biological specimen such as human blood.

As early as 1891, Romanowsky and Malachowski developed mixtures of polychromed methylene blue, azure and methylene violet. Other contributors including names such as Unna (1891), Nocht (1898), Jenner (1899), Leishman (1901), Wright (1902), May-Grunwald and Giemsa (1902), MacNeal (1906) and Lillie (1943) made contributions to what is generally referred to as Romanowsky derived panoptic dye mixtures. The various mixtures developed by the foregoing contributors to advance the state of the art are illustrated in Table I:

TABLE I

| | Eosin | Methylene Blue | Polychromed Methylene Blue | Azure(s) | Methylene Violet |
|---|---|---|---|---|---|
| Romanowsky (1981) | | | X | X | X |
| Malachowski (1891) | | | X | X | X |
| Jenner (1899) | X | X | | | |
| Leishman (1901) | X | | X | | |
| Wright (1902) | X | | X | | |
| Giemsa (1902–04) | X | X | | | |
| MacNeal (1906) | X | X | | X | X |

The state of the art, however, as presently known fails to disclose the use of a single, substantially pure, commercially available azo dye capable of panoptically and metachromatically staining fixed biopsy specimens comprising blood cells, bone marrow cells, or lymph node cells which permit the differentiation, enumeration and identification of the individual cells including leukocytes, and the subpopulations of lymphocytes, megakaryocytes, etc., or any of the abnormal or malignant cells.

The diagnosis of hematological disorders has been achieved, for the most part, by enumeration and identification of formed elements of the peripheral blood and bone marrow. The basis of hematological diagnosis includes the use of light microscopic examination of a panoptically stained specimen of blood cells, lymph node cells, or bone marrow cells. This type of examination provides information sufficient to make a diagnosis which parallels the developments of panoptic light microscopy. Cytochemical stains have been developed to identify cell types more precisely than was possible by using panoptic stains. Cytochemistry represents biochemistry in a microscopic and submicroscopic level. When applied to cells and tissue, cytochemical stains identify enzymes, substrates and organelles. As biochemical probes, cytochemical stains often provide valuable insights regarding aberrations of cellular metabolism. Moreover, cytochemical stains can be selective for one cell type compared to another and therefore such stains have been used in various diagnostic processes especially in making distinctions between various cytological types of acute leukemias and preleukemic disorders.

Concurrent with the development of the synthetic organic dyes, various investigators experimented with supravital stains by adding these dyes to freshly obtained samples of blood or suspension of cells. It was rapidly ascertained that some of the cells were stained with one or more of the dyes whereas other cells were not. Subsequent to the development of supravital staining of blood cells, Ehrlich found the need for a more stable, permanent preparation of blood cells that could be examined under the microscope. Recognizing the difficulties in cell identification in viewing suspensions of unstained cells, Ehrlich devised a stain composed of orange G, acid fuschin and methyl green. On the basis of differential coloration of leukocytes with a mixture of dyes, Ehrlich identified and named most of the blood leukocytes known today. Ehrlich's contribution was remarkable in that by using a plurality of dyes he was able to detect the difference in colors that were distinctive for various cell types. For example, those cells whose granules showed affinity for eosin were called eosinophils. Recognizing that some cells stained differently than the color of the dye in solution, the term metachromasia was popularized and applied to the granules of mast cells. At present, staining techniques form the basis of modern morphological hematology and the nomenclature of various cell types.

Early in the history of the morphologic and cytochemical diagnosis of blood disorders, it was appreciated that examination of only panoptically stained specimens of blood or bone marrow sometimes was not sufficient to make a diagnosis. While some investigators were popularizing supravital stains, others were describing cytochemical stains for blood cells that could be used on dried, fixed preparations of blood or bone marrow. It became apparent that there were some blood cells that had peroxidase activity while other cells did not. The peroxidase test was the first stain that reliably distinguished between granulocytic cells which contain activitiy of peroxidase and lymphoid cells which did not contain peroxidase activity. The peroxidase stains with chromophoric modifications and increased use in immunology remain one of the most useful stains in the cytochemistry of blood cells and is the basis for one of the current automated leukocyte differential counting instruments.

As a staining technique, however, cytochemistry has limitations with respect to age of sample, type of fixative, pH, presence or absence of heavy metal cations, deterioration of the substrate, time and temperature of the staining reaction, etc. These are all variables that affect the cytochemical stain. In addition, any impurities in the organic dyestuff as well as variability in the composition of the dye stuff causes alterations in the staining reaction. However, by using cytochemical stains, it is possible to identify the presence or absence of substances in one cell type contrasted to another or any increase or decrease in the quantity of such substance in those cell types. Quantitatively, these differences assume a diagnostic importance when they reflect differences in one cell type compared to another, and in normal cells compared to abnormal or pathological blood cells.

In several instances, specific diseases have cytochemical profiles that complement the traditional microscopic examination of panoptically stained preparations. There are a variety of hematologic disorders wherein cytochemical tests have diagnostic value. Complementing the conventional light microscopy of panoptically stained specimens of blood or bone marrow, cytochemical stains have improved the precision of hematological diagnosis with the recognition that these stains can reveal properties that are distinctive for one cell type compared to another. Cytochemical stains have found increased application in the study of blood, lymph node and bone marrow specimens. For the most part, these stains detect increased or decreased amounts of an enzyme or a metabolite that reflect the pathophysiological condition of a disordered cell. While the exact mechanism or chemistry responsible for the production of the cytochemical abnormalties are unknown, many of these abnormalities are sufficiently distinctive to make them useful diagnositcally. As a diagnostic tool for cellular hematology, cytochemistry represents a rapid and inexpensive method to distinguish one cell type from another on the basis of characteristic properties. With advances in dye chemistry and the automation of leukocyte counting, one can anticipate further improvements in the cytochemistry of blood cells and the precision of hematological diagnosis in the future. Discussions of cytochemical stains can be found in *New Cytochemical Stains for Blood and Bone Marrow Cells and Cystobiology of Leukemias and Lymphomias*, by L. Kass, M.D., Raven Press, New York, N.Y., Pages 161-177, 1985, and Lawrence Kass, M.D. *Leukemia Cytology and Cytochemistry*, published by J. B. Lippincott, Philadelphia, 1982.

Accordingly, it is an object of this invention to provide a single, substantially pure, water soluble azo dye for use in staining fixed cells of hematopoietic origin.

It is another object of this invention to provide cells of hematopoietic origin fixed and subsequently stained with a water soluble quaternary azo dye to obtain stained cells having individual color characteristics which permit the differentiation, identification and enumeration thereof.

It is a further object of this invention to provide a method of staining a plurality of cells of hematopoietic origin in a fixative to obtain stained cells having individual color characteristics which permit the differentiation, identification and enumeration by means of an instrument. These and other objects will be apparent from a further and more detailed description of the invention as follows.

SUMMARY OF THE INVENTION

This invention is directed to the method of differentiating, identifying and enumerating cells from each other among a plurality of cells of hematopoietic origin selected from the group consisting of blood cells, bone marrow cells, and lymph node cells which comprises fixing said cells in an organic fixative, e.g. as a solution in alcohol which may contain up to about 1.0% of the azo dye and subsequently staining said fixed cells with staining amounts of a water soluble quaternary azo dye, identified in the Colour Index as Basic Blue 41, to obtain a plurality of stained cells. The blood cells, lymph node cells and bone marrow cells of hematopoietic origin may comprise both normal and abnormal cells, i.e. the plurality of cells may comprise malignant cells. The stained cells have individual color characteristics which permit the differentiation, identification and enumeration of each stained cell. The stained cells, with individual color characteristics, may be differentiated by use of various instruments including an image analyzer, microscopes, photomicroscopes, an absorbance light source or any other type of diagnostic instrument.

The cells of hematopoietic origin including blood cells, for example, may be fixed in a variety of fluids known as fixatives. Fixatives are generally classified into two classes based on their ability to coagulate proteins. The coagulant fixatives include, for example, the absolute alcohols such as methanol or ethanol, formaldehyde, trichloroacetic acid, picrics, etc. The ideal fixative should not shrink nor swell the tissue under examination or change the size thereof. However, most fixatives result in some shrinkage or swelling of the tissue. The degree of alteration depends on the nature of the tissue and the fixative employed. In general, anhydrous fixatives such as acetone or absolute alcohols cause shrinkage. A typical example of fixing lymph node tissue is accomplished by using a neutral buffered solution of formalin or absolute alcohols such as methanol. A buffered solution of formalin is an excellent general purpose fixative in that it has the ability to add to the side groups of certain amino acids and thereby denatures the protein and renders it insoluble. Absolute alcohol such as methanol or other anhydrous fixatives are capable of denaturing protein by coagulation and rapid dehydration. Fixatives useful for purposes of this invention, e.g. testing of blood and the like are well known and may be found in the text, incorporated herein by reference, by S. W. Thompson and R. D. Hunt entitled *Selected Histochemical and Histopathological Methods*, published by Charles C. Thomas, Springfield, Ill.

In the process of this invention, the cells of hematopoietic origin are initially exposed to a fixative, e.g., alcohols such as methanol, etc., at ambient temperatures. After washing off the fixative, e.g. with water and/or alcohol etc., the fixed cells are subsequently stained with staining amounts of an aqueous solution of the quaternary azo dye. Preferrably, with an aqueous alkaline buffered solution of the azo dye. Effective amounts of the azo dye needed to stain the fixed cells range up to about 2% and preferrably about 1% by weight of the water soluble quaternary azo dye in solution, e.g. in water alone or in water containing the azo dye and at least one buffering agent. In addition to the above, another preferred method includes fixing the hematopoietically derived cells in a methanolic solution of the dye. The fixed cells are then stained and the characteristic colors are developed by the addition of a buffered alkaline aqueous solution of the quaternary azo dye directly to the methanolic solution of the dye. In another preferred method, the cells are fixed in a methanolic solution of the quaternary azo dye, and then stained with characteristic colors after the addition of an aqueous alkaline buffer solution to the methanolic solution of the quaternary azo dye.

Basophils are particularly visualized with the latter two alternate methods, i.e. basophils require an initial exposure to a methanolic solution of the quaternary azo dye followed by an alkaline buffered aqueous phase that may contain effective amounts of the quaternary azo dye. For optimum staining results, the pH of the aqueous solution of the dyestuff ranges between 7.4 and 7.6.

More specifically, the broad process of this invention is intended to include all of the following variations:

First, a methanolic solution of Basic Blue 41 azo dye is added to cells for 3 minutes. Then an aqueous alkaline buffer is added to the methanolic solution of the dye. After 3 minutes, the slides are washed in aqueous alkaline buffer (e.g. an inorganic phosphate buffer such as Sorensen's buffer pH 7.2-7.6), dried and mounted. Second, a methanolic solution of Basic Blue 41 is applied to cells for 3 minutes. Then an aqueous alkaline buffered solution of Basic Blue 41 azo dye is added directly to the methanolic solution of the Basic Blue 41. After 3 minutes, the cells are washed in alkaline aqueous buffer, dried and mounted. Third, the cells are fixed in absolute methanol for 3 minutes and the methanol is washed with distilled water. Then the cells are stained with an aqueous alkaline buffered solution of Basic Blue 41 azo dye for 3 minutes and washed in alkaline aqueous buffer, dried and mounted.

It is common practice to add the buffering agents to correct the hydrogen and hydroxyl ion concentration of the particular aqueous system. Buffering agents should be used in the lowest possible concentration to adjust the ion concentration of the particular medium. The buffering capacity of a buffering system is referred to as its beta value and is defined as the amount of acid or alkali needed to change the pH by 0.1 unit. Buffering agents are recognized as belonging to several categories incuding a variety of acids, bases and salts. Various mixtures are useful to stabilize the pH values of a particular system or fixative in a biochemical reaction. The desired pH of a particular aqueous system can be obtained by mixing different reagents including various acids, bases or salts such as acetic acid, ammonia acetate, ammonia chloride, ammonia hydroxide, the alkali metal salts such as lithium chloride, lithium hydroxide, sodium hydroxide, potassium hydroxide, the alkali metal phosphates, alkali metal acetates, carbonates, bicarbonates, borates and the like. Buffering systems can be obtained from any of the acids, bases or salts which include the low molecular weight weak organic acids alone or in combination with the alkali metal hydroxide such as citric acid, acetic acid, ethylenediamine tetra acetic acid and the like. Buffering agents useful for purposes of this invention can be found in the text, incorporated herein by reference, by Williams and Chase entitled *Methods in Immunology and Immochemistry*, Vol. II, Academic Press, N.Y. (1968).

The water soluble azo dye used for purposes of this invention is a bright blue substantially pure azo dye identified in the Colour Index as Basic Blue 41 (Colour Index No. 11154). This water soluble azo dye requires no chemical treatment and can be used alone without being mixed with any other dye stuff. It was particularly surprising to discover that only Basic Blue 41 (Colour Index No. 11154) can be used for purposes of this invention as distinguished from its related azo compounds, i.e. Basic Blue 54 (Colour Index No. 11052), Basic Blue 65 (Colour Index No. 11076), Basic Blue 66 (Colour Index No. 11075), and Basic Blue 67 (Colour Index No. 11185). All of these compounds or dyes have substantially the same chemical structure except for the substituent groups and are classified as quaternary water soluble cationic azo dyes. However, only the Basic Blue 41 (Colour Index No. 11154) is operative for purposes of staining hematopoietic cells; see *The Colour Index Revised*, 3rd ed., Vol. 6, first supplement to Vol. 1-4. The azo dye of this invention reacts with the cells resulting in stained cells that have individual Color characteristics, different from the dye, which permit identification of each cell including malignant and parasitic cells. The empirical formula for Basic Blue 41 is characterized by the following:

AZO DYE

No. 11154 - C.I. Basic Blue 41 (Bright Blue)

This single substantially pure azo dye provides a substantial advance in the field of differentiation and identification of hematopoietic cells, i.e. leukocytes and other cells obtained from human biopsy specimens. The HPLC analysis of the azo dye showed no substantial admixture of dyes present in the compound. This particular Basic Blue 41 azo dye is a panoptic dye identified as having unusual properties of metachromasia. The HLPC (high pressure liquid chromatograph) of a commercial grade of the azo dye shows it to be an unusually pure dye of the panoptic class with metachromatic properties as illustrated by the color differences set forth in Table II, wherein each of the seventeen different cells were differentiated and identified by their own color differences.

DETAILED DESCRIPTION OF THE INVENTION

As an illustration, films or smears of peripheral venous blood, including buffy coat preparations as in cases of pancytopenia, subleukemic leukemia, acute leukemia or bone marrow particles obtained by sternal or iliac puncture, or blood smears in parasitic studies were prepared between glass cover slips or on clean glass slides. The cover slips or glass slides were air dried, fixed for a period of about 2 minutes in a 1% by weight solution of the Basic Blue 41 quaternary azo dye in absolute methanol. Next, a 1% aqueous solution of the dye buffered to pH 7.6 by the addition of Tris maleate 200 millimole per liter was added in an equal volume to the methanolic solution of the dye already in contact with the cells. After a period of 2 to 3 minutes, these stained specimens were subsequently washed with an alkaline aqueous buffer, e.g. inorganic phosphate buffer such as Sorensen's at pH 7.2-7.4, at ambient temperatures until bleeding of the azo dye from the prepared slides could not be detected. The washed slides or coverslips were mounted, face down on clean glass slides with a conventional mounting medium.

As an alternative method, glass slides or coverslips containing cells were fixed in a methanolic solution of Basic Blue 41 for about three minutes. Then, an equal volume of pH 7.2 buffer, e.g. Sorensen's, was added directly to the methanolic solution of the dye already in contact with the cells. The addition of this aqueous phase initiated the staining reaction and produced the characteristic colors. After three minutes, slides were washed in the aqueous alkaline buffer, air dried and mounted.

The stained specimens were examined under white light microscopy. Other types of instruments may be employed as the technology advances to provide various automatic differential analyzers or instruments. One of the advantages in using the quaternary azo dyes of this invention is that the films and smears are capable of being preserved and reexamined over long periods of time. This stability of the stained specimens provides the capability of storing records over long periods of time which can be periodically reviewed and studied without concern of deterioration. The shelf life or stability of a 1% aqueous solution or methanolic solution of the Basic Blue 41 azo dye appears to be excellent. The dye in powder form has an indefinitely long storage life.

By comparing the azo Blue Dye 41 of this invention with conventional panoptic staining dye mixtures, the following advantages were observed. There was a more rapid staining which eliminates the time required by the conventional panoptic stains and only one substantially pure single lot of the dye is required rather than several lots of different dye stuffs. Therefore, there is better quality control with a single azo dye as compared with mixtures of dyes wherein the variation in proportions inherently cause a variation in control and performance.

In comparison to the conventional Romanowsky stains, the Basic Blue 41 azo dye of this invention provides a clearer detail of nuclear chromatin, and more a brilliant coloration of the granules. For example, the identification of established populations of leukocytes including the T-cells, B-cells and related subpopulations of lymphocytes, i.e. the T-suppressor cells, T-helper cells and natural killer cells which are known to be important modulators or modifiers of the immune response in normal individuals can now be identified without delay. The identification, differentiation and enumeration of the populations and sub-populations of lymphocytes including the T-cells and B-cells, which are the major lymphocyte population in man, are basic to the understanding of the immune system and the various diseases such as lymphomas, leukemia, and immunodeficiency problems.

B-cells represent about 10 to 20% of the peripheral blood lymphocytes. T-cells which are indicators of the cellular immune responses, i.e. delayed hypersensitivity and graft and organ transplant rejection constitute about 70 to 80% of the total. Sub-populations of the lymphocytes known as T-helper cells, and T-suppressor cells, serve to regulate antibody production and are effectors of T-cell function. Enumeration of T-lymphocytes has diagnostic significance in certain chronic disorders where reduced numbers are found. Monitoring the number of T-suppressor and T-helper cells has advanced the understanding and treatment of diseases affecting the immune system. Changes in the ratios of T helper or T-suppressor cells has been noted as being important in allergy characterization. Monitoring relative changes in these numbers is an indication of a possible rejection in organ surgery transplant.

Chemotherapy patients have been monitored to maintain an immuno-competent state in guiding improvements in the prognosis of cancer patients. Chronic lymphocytic leukemia was often characterized by a monoclonal proliferation of B-cells. More recently, T-helper variant, T-suppressor variant and natural killer cell variant have been observed wherein leukemic lymphocytes share surface antigenic properties found in the corresponding normal lymphocyte sub-type. Changes in the ratio of T-helper cells to T-suppressor cells have been frequently found in AIDS (Acquired Immune Deficiency Syndrome). Natural killer cells are postulated to constitute the body's first line of defense against carcinogenic influences. To date, there is no established, reproduceable method for identifying the differences between B-cells, T-suppressor cells, T-helper cells and Natural Killer or NK cells with any known panoptic stain. There is no method available for using a single stain of megakaryocytes to identify, distinguish or enumerate these cells from among all other cells in a formalin-fixed biopsy section. Staining of parasitic cells, i.e. cells which contain and/or are surrounded by parasites, in the blood are also accurately delineated. Parasites from individuals known to be victims of parasitic attack such as in tropical fevers, i.e. malaria, due to Plasmodium Falciparum and Trypanosomiasis can be identified by their specific color and patterns. Sharper contrasts have been noted with the pure Blue 41 azo dye making clear diagnoses more accurately. Basic Blue 41 produces substantially the same coloration of the parasites, but the detail is obtained quicker and with greater clarity of results.

Figure 1A:
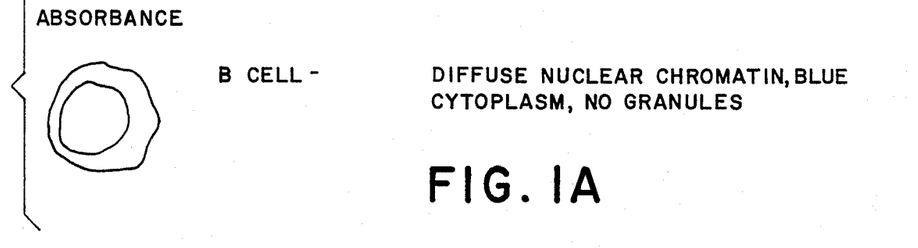
Figure 1B:
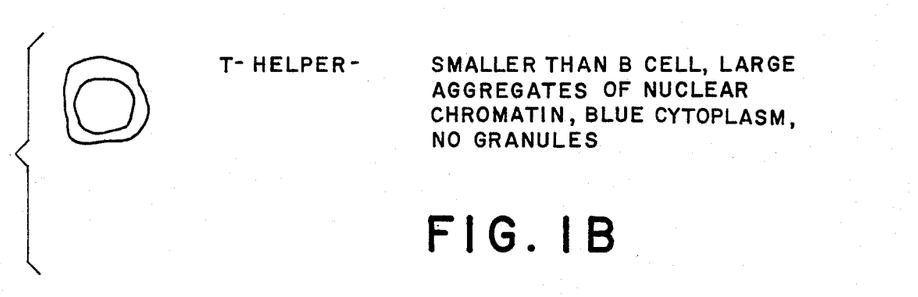
Figure 1C:
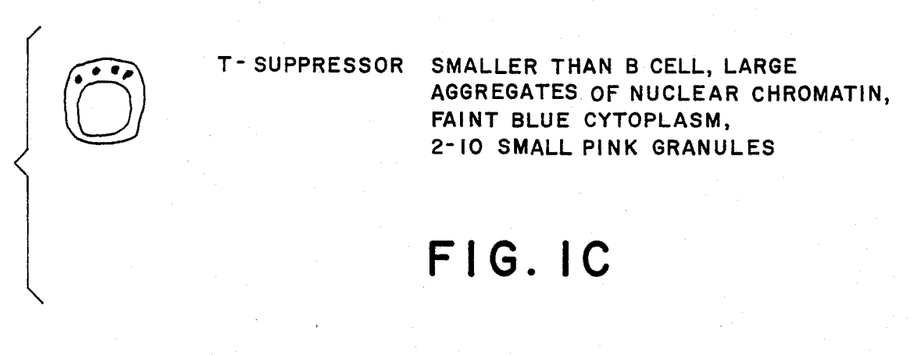
Figure 1D:
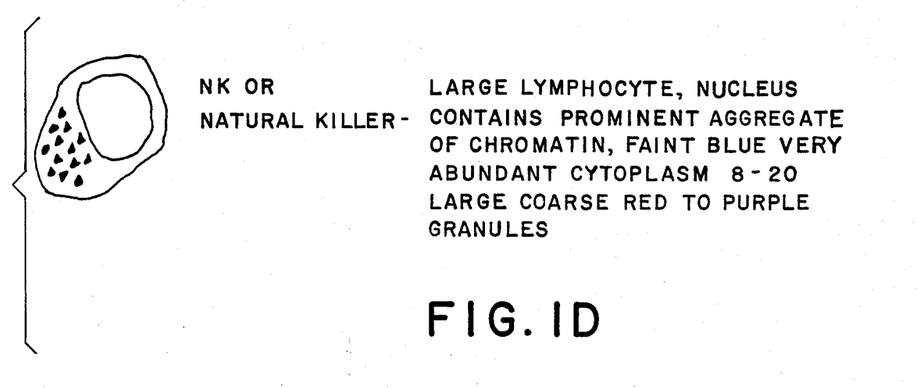

FIGS. 1A, 1B, 1C and 1D of the drawing illustrates the cell classification relative to the sub-populations of lymphocytes including the B-cells, T-cell, T-suppressor and Natural Killer cells.

The method of identifying, enumerating and differentiating a plurality of cells of hematopoietic origin are illustrated by Table II.

TABLE II

| CELL | NUCLEUS | CYTO-PLASM | GRANULES |
| --- | --- | --- | --- |
| 1. Erythrocytes | — | pale green | — |
| 2. Platelets | — | lavender | red, purple |
| 3. Neutrophils | red, brown | cream color | red, brown |
| 4. Lymphocytes | red, brown | pale blue | rare red |
| 5. Monocytes | red, brown | lavender | red, pink |
| 6. Eosinophils | red, brown | colorless | bright green |
| 7. Basophils | red, brown | colorless | red-purple |
| 8. Megakaryocytes | red, brown | purple | red, crimson |
| 9. Plasma cells | red, brown | blue | — |
| 10. Macrophage | red, brown | gray | yellow, brown, green |
| 11. Proerythroblasts | red, brown | deep blue | — |
| 12. Normoblasts | red, brown | blue-gray-green | — |
| 13. Promyelocytes | red, brown | blue | orange, red |
| 14. Neutrophilic Myelocytes | red, brown | yellow | orange, red |
| 15. Neutrophilic Metamyelocytes | red, brown | yellow | orange, brown |
| 16. Band | red, brown | cream color | orange, brown |
| 17. Mast cells | red, brown | colorless | red-purple |

In the erythroblast series, the range in color is from blue in the earliest erythroblast cytoplasm to gray-green in the cytoplasm of later normoblasts which reflect increasing hemoglobinization of the cell (green color). Maturation of granulocytic cells in the neutrophilic series, from promyelocyte to band, is reflected by the difference in size, cytoplasmic volume, nuclear configuration, and the number and color of granules (primary granules stain orange and red, whereas secondary granules stain brown).

While this invention was conceived through optical microscope study and through individual laboratory research, it is well-known in the medical diagnostics arts that optical microscopes have been and are supplanted by many technical advances wherein laser techniques and computer-type instrumentation, for example, have been used to supercede and advance identification, differentiation and enumeration of the normally invisible by improved instrumentation. Thus, the term microscopic as used herein is generic to the universe of the infinitely small.

In certain chronic disorders patients may be found generally to have reduced numbers of T-lymphocytes. More recently, it has been found advantageous to monitor subset numbers in analysis of $T(_s)$ and $T(_h)$ subsets of T-cell numbers as an aid to understanding and treatment of diseases affecting the immune system. Allergies may be characterized by changes in ratio of T-helper and T-suppressor subset numbers. Monitoring the changes in these numbers may provide an indication of a rejection arising in organ transplant surgery. Chemotherapy patients have been monitored as an aid to the physician in maintaining an immuno-competent state in guiding improvements in the prognosis of cancer patients. Severe combined immuno-deficiency diseased patients suffering from decreasing B-cell and T-cell lymphocytic function may be aided by bone marrow transplantation through such clinical studies of the immune system.

Studies performed in research laboratories relating to immunological research presently rely upon immunologic markers to identify specific lymphocyte sub-populations. T and B-cells were the first lymphocyte sub-populations to be so identified. The state of the art has now reached the point where T and B cell assays are routine in cytochemical examination, presently by use of the reaction of monoclonal antibodies, and earlier by use of the reaction for acid phosphatase.

Over the past several decades, it has become apparent that lymphocytes, once thought to be a single class of cells, are actually a heterogeneous collection of multiple sub-populations. Early studies established that there were at least two major types of lymphocytes in blood and in lymph nodes, namely T and B-cells. T-cells are believed to be involved in cell-mediation immunity, and constitute the largest number of lymphocyte in normal peripheral blood. B-cells are involved in humoral immunity and in the synthesis of antibody, and constitute a small proportion of the total number of lymphocytes in normal blood. At first, T and B-cells were distinguished from one another on the basis of their ability to form rosettes with sheep erythrocytes. B-cells formed rosettes with sheep red blood cells treated with complement. T-cells formed rosettes with untreated sheep red blood cells. In lymph nodes, B-cells are found predominantly in the germinal center of lymphoid follicles. T-cells are the predominant type of lymphocyte in the paracortical regions.

Shortly after the separation of lymphocytes into T and B-cell types, it became apparent that some lymphocytes were neither T or B-cells and accordingly were null cells. In an effort to more precisely characterize the properties of T and B-cells, various enzymatic and cytochemical techniques were applied to lymphocyte suspensions. Using this reaction for acid phosphatase, it was found that T-cells contained unipolar localization of the reaction product, whereas B-cells contained little, if any, activity of acid phosphatase. Similarly, nonspecific esterase activity is localized in a unipolar distribution of reaction product in T-cells, but in B-cells nonspecific esterase activity is diffuse or absent.

Another milestone in the detection of lymphocyte sub-populations occurred approximately a decade ago. Specific monoclonal antibodies against cell surface antigens were synthesized using newly developed immunologic techniques for antibody production. Soon, a wide variety of specific cell surface antibodies were developed for lymphocytes, and applied to the problem of lymphocyte identification. With this new technology, multiple sub-populations of lymphocytes were detected, based upon their cell surface properties. These sub-populations included B-cell, T-cell, T-helper cell, T-suppressor cell, and natural killer (NK) cell.

Concurrent with these developments, greater understanding of the role of the lymphocyte sub-populations in health and disease was taking place. Chronic lymphocytic leukemia was characterized as a monoclonal proliferation of B-cells, in most instances. More recently, other variants of chronic lymphocytic leukemia and of lymphocytic lymphoma have been described. In the case of chronic lymphocytic leukemia, these include a T-helper variant, T-suppressor variant, and natural killer variant, in which the leukemic lymphocytes share surface antigenic properties found in the corresponding normal lymphocyte sub-type.

Additional studies indicated that in normal individual, T-helper and T-suppressor cells acted as modulators or modifiers of the immune response. In systemic lupus erythematosis and in rheumatoid arthritis elevated levels of T-helper cells were found. In infectious mononucleosis, the atypical lymphocyte was characterized as T-suppressor cell. Within the past several years, changes in the ratio of T-helper cell to T-suppressor cell in the peripheral blood have been described as a frequent finding in patients with the Acquired Immune Deficiency Syndrome (AIDS). Currently, the finding of elevated levels of T-suppressor cells and either normal or reduced numbers of T-helper cells is one of the few diagnostic tests available for detection of patients with AIDS and individuals at risk for development of AIDS.

Natural killer cells (NK) have been subjects of active interest in many laboratories around the world for the past several years. Natural killer cells correspond to the large granular lymphocyte seen with conventional panoptic stains like Wright's or Giemsa's stain, and the granules are believed to be lysosomes since they contain phosphatase. Although the role of natural killer cells is not fully understood at the present time, these cells are believed to constitute the body's first line of defense against malignancy. Natural killer cells are able to directly kill a foreign or invading malignant cell without the mediation of complement. In parallel with developments in immunology, development of instrumentation, such as the fluorescence activated cell sorter, has also progressed rapidly and provides a powerful analytical tool for separation of the lymphocyte sub-populations in a higher purified form.

Although natural killer cells have been equated with large granular lymphocytes as visualized with conventional panoptic stains, as yet there has not been a description or reproducible differences between B-cells, T-suppressor cells, T-helper cells, and natural killer cells with any panoptic stain. At present, differences between the lymphocyte sub-populations are detectable only with the use of monoclonal antibodies using tedious and expensive techniques, or with the less highly specific methods such as sheep red cell rosetting.

The following examples are specific illustrations of using Basic Blue 41 in the practice of the invention.

EXAMPLE 1

A male patient, age 40, developed weakness and fever. Physical examination revealed an enlarged spleen. Laboratory studies further showed hemoglobin 9 grams %, white blood cell count of 278,000/mm$^3$ and a platelet count of 684,000/mm$^3$. A series of films or smears of peripheral venous blood and bone marrow particles were made between cleaned glass coverslips for film preparations and on cleaned glass slides for smears. After air drying, the specimens were fixed for three minutes in a methanolic solution of Basic Blue 41 at room temperature (25° C.) followed by addition of a pH 7.2 phosphate buffer to one methanolic solution of the dye.

After three minutes, the so prepared fixed coverslips and slides were washed with aqueous alkaline buffer, e.g. Sorensen's buffer at pH 7.2–7.4, until no further bleeding of the dye color from the slide was observed. The water-washed slides and coverslips were again air dried. The coverslips were mounted face down on cleaned glass slides with conventional synthetic resin mounting media. These were then subject to white light illumination and microscopic examination.

The permanent slides so prepared exhibited a striking increase over normal in mature and immature granulocytic cells and increased number of basophils. Diagnosis of chronic granulocytic leukemia was confirmed by the presence of the Philadelphia chromosome upon further cytogenetic analysis of the bone marrow.

EXAMPLE 2

A 78 year old female noticed sores in her mouth and bleeding gums. Routine blood count determined hemoglobin of 8 grams %, white blood cell count 3500/mm$^3$ with 65% monocytes, platelet count 4000/mm$^3$.

Peripheral blood and bone marrow films fixed and then stained with a 1% solution of Basic Blue 41 in distilled water and were further prepared as in Example 1. Increased numbers of monocytes possessing red-brown staining of nuclear chromatin, nuclear lobulations and abundant cytoplasm that stained pale lavender containing variable numbers of red and pink granular structures were observed. A duplicate set of slides separately prepared from the patient's blood using Wright's stain (prior art) revealed monocytes stained similarly to the above blood stained slides in hue and chroma using Basic Blue 41. The above dual analyses were confirmatory consistent with a finding of acute myelomonocytic leukemia.

EXAMPLE 3

An 18 year old male college student developed fever, enlarged cervical lymph nodes and pharyngitis. Physical examination revealed a tender, enlarged spleen. Laboratory studies showed hemoglobin 13 grams %, white blood cells 25,000/m$^3$ and platelets of 175,000/mm$^3$.

Peripheral blood smears prepared as in Example 1 using an aqueous 1% solution of Basic Blue 41 determined 80% atypical lymphocytes. These contained a red-brown stained nucleus with block-like aggregates of nuclear chromatin and abundant cytoplasm staining pale blue in some lymphocytes. Other lymphocytes were observed staining a brighter blue with radial striation. A similar slide made at the same time using Wright's stain, a standard prior art panoptic staining mixture, produced atypical lymphocytes having substantially similar hues and chromas as had been first perceived using Basic Blue 41, confirming the factual basis for diagnosis. As confirmed by serological testing, the diagnosis was infectious mononucleosis.

EXAMPLE 4

A 49 year old male had no detectable abnormalities upon physical examination. On routine laboratory analysis he was found to have an elevated white blood cell count (white blood cell count 22,000/mm$^3$), hemoglobin 14 gram %; and platelets 250,000/mm$^3$.

Slides prepared as in Example 1 consisting of peripheral blood smear and bone marrow smear stained with Basic Blue 41, aqueous, were examined under white light microscopy. Found were approximately 80 to 90% mature lymphocytes identified by red-brown staining nuclei containing well defined aggregates of nuclear chromatin and pale blue agranular cytoplasm. As confirmed by a Wright's stained slide made at the same time, the diagnosis was chronic lymphocytic leukemia.

EXAMPLE 5

During physical examination a 56 year old woman reported fever and abdominal pain. The locus of the pain was the right lower quadrant. Intestinal perforation was indicated by X-ray of the abdomen showing free air. Hemoglobin was 10 grams %, white blood cell count 38,000/mm³ and platelet count 450,000/mm³. A peripheral blood smear and a smear of bone marrow particles obtained by a biopsy were fixed as in Example 1 and stained with an 1% aqueous solution of Basic Blue 41.

Microscopic examination of the above repared Permount slides established increased numbers of bands having cream color cytoplasm and orange-brown granules. Neutrophils showed a segmented nucleus that stained red-brown, and cream colored cytoplasm containing red and brown granules.

Except for lack of nuclear segmentation, the bands were similarly responsive to the stain indicia as were the neutrophils. Metamyelocytes had kidney-bean shaped nucleus, stained red-brown; a yellow cytoplasm containing orange and brown granules was noted. Myelocytes exhibited a round to oval red to brown stained nucleus and a yellow cytoplasm containing orange and brown granules. Promyelocytes had similar shape and color nucleus, but the cytoplasm stained blue with orange and red colored granules.

Similarly prepared comparative slides using Wright's stained biopsy specimens of the patient's blood and bone marrow upon comparison with the above demonstrated substantially the same hue and chromas as reported above. However, erythrocytes stained with Basic Blue 41 were pale green, while with Wright's stain were orange in color. This is indicative of the affinity of the hemoglobin of the erythrocytes for eosin found in Wright's plural dye containing panoptic staining mixtures. As confirmed by Wright stained slides of blood and bone marrow made at the same time, the diagnosis of probable leukemoid reaction was made. After removal of a perforated appendix, the blood abnormalities disappeared.

EXAMPLE 6

Exacerbation of broncial asthma of a 32 year old female admitted her to the hospital. Frequent wheezing of the chest was observed. Laboratory studies report hemoglobin 13 grams %; white blood cell count 15,000/mm³; platelet count 325,000/mm³.

A peripheral blood smear stained with a solution (1%) Basic Blue 41 dye in distilled water established the presence of 30 to 40% eosinophils. Microscopic identification was characterized by a bi-lobed red-brown staining of the nucleus. The cytoplasm was filled with bright green stained oval to round granules. (Wright's stained granules of eosinophils ran in comparison were orange, again indicating affinity of the granules for the eosin component of the plural dye mixture of this panoptic stain.)

EXAMPLE 7

An 80 year old man was admitted to the hospital complaining of profound weakness and fatigue. On physical examination he was pale and vital signs were normal. Laboratory data included hemoglobin 9 grams %; white blood cell count 22,000/mm³, and platelet count 650,000/mm³. Peripheral blood film stained with Wright's stain and a separate film stained with Basic Blue 41 both revealed increased numbers of platelets with many giant bizarre appearing platelets. Increased numbers of immature white blood cells (promyelocytes, myelocytes, metamyelocytes) and nucleated red blood cells were seen, along with tailed poikilocytes. Attempts at aspiration of bone marrow resulted in a "dry tap", but a bone marrow biopsy fixed in B5-formalin and sectioned in the usual way showed hypercellularity, increased fibrosis, and increased numbers of megakaryocytes using an H and E (hemotoxylin and eosin) stain. Using a 0.1% aqueous solution of Basic Blue 41 as a stain on a separate slide, megakaryocytes stained bright pink, whereas all other one marrow cells stained pale blue. Using Basic Blue 41, megakaryocytes were easily and immediately visible as a result of their distinct color compared to other marrow cells, and their number could be readily quantitated. A diagnosis of agnogenic myeloid metaplasia with myelofibrosis was made.

EXAMPLE 8

A 55 year old woman was admitted to the hospital because of red spots on her lower legs, occuring over a period of 48 hours prior to admission. On physical examination, she was pale. The skin of both lower legs showed multiple petechiae. The tip of the spleen was palpable. Laboratory values included hemoglobin 12 gram %, white blood cell count 13,000/mm³, and platelet count 3,000/m³. Wright's stained, as well as separately Basic Blue 41 stained coverslips of peripheral blood, showed normal appearing white blood cells but striking decrease in the number of platelets. Bone marrow aspiration stained with either Wright's stain or Basic Blue 41 demonstrated increased numbers of young appearing megakaryocytes. On bone marrow biopsy fixed in B5-formalin and section in the usual way, H and E stain showed increased numbers of megakaryocytes. However, a separate section of bone marrow biopsy stained with Basic Blue 41 demonstrated striking numbers of megakaryocytes that stained bright pink, whereas all other bone marrow cells stained pale blue. A diagnosis of idiopathic thrombocytopenic purpura (ITP) was made.

EXAMPLE 9

In another series of examples the aqueous blue stain solution comprising Basic Blue 41 was applied to a series of human bone marrow biopsies, fixed in B5-formalin, embedded in parrafin, and sectioned on a microtome. Here, Basic Blue 41 was established as a selective stain for megakaryocytes which cells stained a bright pink, while all other bone marrow cells stained blue. The test were performed as follows:

Paraffined sections of bone marrow, spleen and lymph nodes were conventionally prepared, brought to water after successive rehydration exposures through a series of concentrations from absolute alcohol dilutions.

Rehydrated sections were stained for 2 minutes with a 0.1% aqueous solution of Basic Blue 41. After washing in distilled water, the sections were immersed briefly in a series of alcohols of increasing alcohol concentration to dehydrate and then immersed in xylene.

A glass coverslip was applied over the tissue section with Permount.

Upon study under a light microscope of the several slides so prepared, megakaryocytes of varying maturational ages in both health and disease demonstrated bright pink staining of the cytoplasm. No other cell in the specimens stained this color. Other marrow cells stained blue. In sections known to contain other giant type cells including osteoclasts, Reed-Sternberg cells and Laughans giant cells, pink staining of the cytoplasm did not occur. Megakaryocytes, which stained bright pink, were identified, differentiated and enumerated easily.

EXAMPLE 10

Of interest was a series of tests where diastase was used to remove glycogen or ribonuclease to remove DNA, staining of megakaryocytes with Basic Blue 41 was not impaired. However, upon removal of acid mucopolysaccharide with hyaluronidase the pink color of the cytoplasm of the megakaryocytes failed to develop.

EXAMPLE 11

A 75 year old white male was admitted to the hospital with fever and chills. On physical examination, temperature was 103.5° F. He had enlarged lymph nodes and an enlarged spleen. Laboratory studies revealed hemoglobin 10.2 grams %, white blood cell count 8,500/mm$^3$, and platelet count 100,000/mm$^3$. Using Wright's stain, a differential count on a peripheral blood film showed approximately 85% lymphocytes and 15% neutrophils.

Using Basic Blue 41, the peripheral blood film revealed 85% lymphocytes and 15% neutrophils, and the lymphocytes were medium sized with diffuse nuclear chromatin and basophilic cytoplasm devoid of granularity. With a more tedious immunoperoxidase stain, the lymphocytes were confirmed as B-cells. diagnosis: Chronic Lymphocytic Leukemia.

EXAMPLE 12

A 32 year old black female was admitted to the hospital with a two week history of ankle edema, shortness of breath, and visual loss. On physical examination, vital signs were normal. An erythrematous facial eruption along with an enlarged spleen was noted. Funduscopic examination disclosed multiple small white blood cell count 15,000/mm$^3$, and platelet count 65,000/mm$^3$. A differential cell count on a peripheral blood film stained with Wright's stain showed a normal differential with normal appearing lymphocytes. A differential cell count on the peripheral blood stained with Basic Blue 41 showed increased numbers of small lymphocytes, corresponding to T-cells. Also, the small lymphocytes having deep basophilic cytoplasm and no visible granules comprising approximately 70% of the total number of small lymphocytes. With immunoperoxidase staining, approximately 70 to 75% of the small lymphocytes were identifiable as T-helper cells. Other laboratory data included a positive ANA test and a positive LE cell test. Diagnosis: Systemic Lupus Erythrematosis.

EXAMPLE 13

A 28 year old white male was admitted to the hospital with a one month history of cough, fever, lymphadenopathy, and weakness. On physical examination, he was pale, and vital signs were normal. Enlarged lymph nodes were found in the cervical, inguinal, and axillary areas. Laboratory data included hemoglobin 10 gram %, white blood cell count 14,500/mm$^3$, and platelet count 125,000/mm$^3$. Wright's stained peripheral blood differential revealed normal numbers of lymphocytes, and no obvious differences between lymphocytes could be ascertained. On a peripheral blood film stained with Basic Blue 41, the majority of the lymphocytes were small, and of these small lymphocytes, approximately 60% had 6 to 10 tiny pink granules. Upon immunoperoxidase staining, these small lymphocytes corresponded to T-suppressor cells, creating an inversion of the normal T-helper/T-suppressor ratio. These laboratory and clinical findings were consistent with the diagnosis of Acquired Immune Deficiency Syndrome (AIDS). Subsequently, the patient expired with an opportunistic infection.

EXAMPLE 14

A 25 year old white male serviceman on leave to U.S.A. after a tour of duty in southeast Asia, was admitted with fever and chills of 3 days duration. Physical examination revealed a pale skin, BP120/70, pulse 100, temperature 104° F. An enlarged spleen could be felt in the abdomen. Laboratory values included hemoglobin 10 grams %, white blood cell count 22,000/mm$^3$ with increased numbers of neutrophils and bands, platelet counts 425,000/mm$^3$. Bilirubin was 3.2 mg %.

A thick smear of peripheral blood stained with Giemsa's stain revealed parasitic infestation of erythrocytes with the malarial parasite Plasmodium Falciparum. A comparative duplicated thick blood smear stained rapidly with Basic Blue 41 revealed unusually vivid coloration of malarial parasites with colors substantially identical to those seen with the prior art Giemsa's stain. Malaria was diagnosed with accuracy and dispatch.

EXAMPLE 15

In another similar case to the foregoing, the parasite causing Trypanosomiasis stained red-purple in a blood smear and was readily identified with Basic Blue 41. Confirmation was made with use of Romanowsky dye.

EXAMPLE 16

Using 125 cc of normal human blood from normally healthy volunteers, Ficoll-Hypaque gradients were used to isolate lymphocytes. The isolated lymphocytes were then treatd with specific lymphocytic antigens, and separated into highly purified fractional populations by means of a commercial fluorescence activated cell sorter. B-cells were identified with anihuman total immunoglobulin Fab$_2$ fragment, OKT-4 for T-helper cells, OKT-8 for T-suppressor cells and Leu 7 for natural killer cells. After sorting, the lymphocytes were isolated to about a 95% purity according to their subpopulations. After the sorting step, the fractions were further concentrated with a cytocentrifuge. Each one of the so concentrated, purified lymphocyte sub-populations were deposited on separate clean glass slides, air dried and further fixed with a 1% solution of the Basic Blue 41 dye (C.I. 11154) in absolute methanol for 2 minutes. Without washing, a 1% aqueous solution of Basic Blue 41 buffered with tris maleate to pH 7.6 was added, and stained for 2–3 minutes with the buffered dye. Wash with aqueous alkaline buffer at pH 7.2 to remove all excess dye, air dry and mount on a clean glass slide for conventional light microscopy.

B-lymphocytes stained with Basic Blue 41 were large lymphocytes with basophilic agranular cytoplasm. The nuclei contained diffuse appearing chromatin with apparently smooth aggregates. Occasionally, one noted the nuclei of the B-cells to be eccentrically placed with the cell having some resemblance to plasma cells (See FIG. 1). T-helper cells were smaller than the B-cells with large, darkly stained nucleus chromatin with prominent block-like aggregates of chromatin within the nucleus, the cytoplasm being free from granules and a deeply basophilic blue. The T-suppressor cells were also small lymphocytes of the same general size of the T-helper cells with darkly stained nuceli containing prominent block-like aggregates of nuclear chromatin and scant less deeply blue cytoplasm. A prominent difference over the T-helper cells the T-suppressor cells (identified with the OKT-8 antiobdy contained 2 to 8 pink to red granules in the cytoplasm). The NK cells (natural killer cells) were observed to be unusually large lymphocytes containing large round to oval nucleus containing both diffuse and block like aggregates of chromatin and a noticeably more voluminous or abundant cytoplasm than the cells described above containing a generally increased number of from about 4 to 20 larger or coarser red to purple stained granules.

While this invention has been described by a specific number of examples, it is obvious that there are a number of variations and modifications which can be resorted to without departing from the scope of the invention as particularly set forth in the appended claims.

The invention claimed is:

1. A method for differentiating, identifying and enumerating cells from each other among a plurality of cells of hematopoietic origin selected from the group consisting of blood cells, bone marrow cells and lymph node cells which comprises fixing said cells in an organic fixative and subsequently staining said fixed cells with a staining amount of a water soluble quaternary azo dye, identified as Basic Blue 41, (C.I. 11154) to obtain a plurality of stained cells; said stained cells having individual color characteristics which permit the differentiation, identification and enumeration of each cell.

2. The method of claim 1 further characterized in that the stained cells have color characteristics which permit the differentiation, identification and enumeration by use of an absorbance light source.

3. The method of claim 1 further characterized in that the stained cells have color characteristics which permit the differentiation, identification and enumeration by use of an image analyzer.

4. The method of claim 1 further characterized in that the cells of hematopoietic origin are blood cells.

5. The method of claim 1 further characterized in that the cells of hematopoietic origin are lymph node cells.

6. The method of claim 1 further characterized in that the cells of hematopoietic origin are bone marrow cells selected from the group consisting of erythrocytes, platelets, neutrophils, lymphocytes, monocytes, eosinophils, basophils, megakaryocytes, plasma cells, macrophage, proerythroblasts, normoblasts, promyelocytes, neutrophilic myelocytes, neutrophilic metamyelocytes, bands, and mast cells.

7. The method of claim 1 further characterized in that the fixative comprises a lower molecular weight alcohol.

8. The method of claim 1 further characterized in that the fixative comprises formaldehyde.

9. The method of claim 7 further characterized in that the alcohol fixative contains up to about 2.0% by weight of the azo dye in solution.

10. The method of claim 9 further characterized in that the fixed cells are stained by the addition of an aqueous solution of an alkaline buffering agent to the alcohol solution of fixed cells.

11. The method of claim 7 further characterized in that the cells are fixed in the alcohol and then stained by the addition of staining amounts of an aqueous solution of the azo dye to the alcohol.

12. The method of claim 11 further characterized in that an effective amount of a buffer agent is added to the aqueous solution of the azo dye to increase the pH.

13. The method of claim 12 further characterized in that an effective amount of am alkaline buffering agent is added to the aqueous solution of azo dye to increase the pH of the aqueous solution above 7.

14. The method of claim 9 further characterized in that the water soluble azo dye is present in the alcohol fixative in staining amounts ranging up to about 1.0% by weight.

15. The method of claim 10, further characterized in that the water soluble azo dye is present in the aqueous solution of buffering agent in staining amounts ranging up to about 1.0% by weight.

16. The method of claim 9 further characterized in that the water soluble azo dye is present in a fixative of absolute methyl alcohol in staining amounts ranging up to about 1% by weight.

17. The method of claim 1 further characterized in that the cells of hematopoietic origin are fixed in a solution of absolute methyl alcohol and then stained with staining amounts of an aqueous solution of the water soluble quaternary azo dye.

18. The method of claim 17 further characterized in that the aqueous solution of the water soluble quaternary azo dye containing effective amounts of buffering agent, are added to a solution of the cells in the organic fixative at ambient temperatures.

19. The method of claim 17 further characterized in that the buffering agent is present in an amount sufficient to increase the pH of the aqueous solution of the quaternary azo dye above 7.

20. The method of claim 19 further characterized in that the cells of hematopoietic origin are human blood cells.

21. The method of claim 1 further characterized in that the cells of hematopoietic origin are bone marrow cells selected from the group consisting of erythrocytes, platelets, neutrophils, lymphocytes, monocytes, eosinophils, basophils, megakaryocytes, plasma cells, macrophage and proerythroblasts.

22. The method of claim 1 further characterized in that the cells of hematopoietic origin are blood cells selected from the group consisting of monocytes, platelets, eosinophils, basophils, B-lymphocytes, T-suppressor cells, T-helper cells, and Natural Killer cells.

23. The method of claim 1 further characterized in that the cells of hematopoietic origin are lymph node cells selected from the group consisting of B-lymphocytes, T-suppressor cells, T-helper cells and Natural Killer cells.

24. The method of claim 1 further characterized in that the cells of hematopoietic origin comprise cells containing and surrounded by parasites.

25. The method of claim 1 further characterized in that the blood cells of hematopoietic origin comprise malignant cells.

26. The method of claim 1 further characterized in that the lymph node cells of hematopoietic origin comprise malignant cells.

27. The method of claim 25 further characterized in that the stained cells have color characteristics which permit the differentiation, identification and enumeration by use of an image analyzer.

28. The method of claim 25 further characterized in that the color characteristics permit the differentiation, identification and enumeration by use an of absorbance light source.

29. The method of claim 25 further characterized in that the color characteristics permit the differentiation, identification and enumeration by use of a microscope.

* * * * *